US007076298B2

(12) United States Patent
Padmanabhan et al.

(10) Patent No.: US 7,076,298 B2
(45) Date of Patent: Jul. 11, 2006

(54) METHOD AND APPARATUS FOR PREVENTION OF ARRHYTHMIA CLUSTERS USING OVERDRIVE PACING

(75) Inventors: Vasant Padmanabhan, Maple Grove, MN (US); Walter H. Olson, North Oaks, MN (US); Rahul Mehra, Stillwater, MN (US); Xiaohong Zhou, Plymouth, MN (US); Thomas J. Mullen, Ham Lake, MN (US); William J. George, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 723 days.

(21) Appl. No.: 10/171,231

(22) Filed: Jun. 14, 2002

(65) Prior Publication Data
US 2003/0233130 A1    Dec. 18, 2003

(51) Int. Cl.
*A61N 1/36*    (2006.01)
(52) U.S. Cl. .................. 607/14; 600/515; 607/9
(58) Field of Classification Search ......... 600/515–518
See application file for complete search history.

(56) References Cited

U.S. PATENT DOCUMENTS

| 4,316,472 A | 2/1982 | Mirowski et al. ....... 128/419 D |
| 4,375,817 A | 3/1983 | Engle et al. ............ 128/419 D |
| 4,384,585 A | 5/1983 | Zipes .................... 128/419 D |
| 4,577,633 A | 3/1986 | Berkovits et al. ..... 128/419 PG |
| 4,587,970 A | 5/1986 | Holley et al. ......... 128/419 PG |
| 4,726,380 A | 2/1988 | Vollmann et al. ..... 128/419 PG |
| 4,727,877 A | 3/1988 | Kallok ................... 128/419 D |
| 4,800,883 A | 1/1989 | Winstrom ............... 128/419 D |
| 4,830,006 A | 5/1989 | Haluska et al. ....... 128/419 PG |
| 4,880,005 A | 11/1989 | Pless et al. .......... 128/419 PG |
| 4,949,719 A | 8/1990 | Pless et al. ............ 128/419 D |
| 4,953,551 A | 9/1990 | Mehra et al. .......... 128/419 D |
| 5,048,521 A | 9/1991 | Pless et al. .......... 128/419 PG |
| 5,058,599 A | 10/1991 | Andersen ................ 128/705 |
| 5,086,772 A | 2/1992 | Larnard et al. ........ 128/419 D |
| 5,107,850 A | 4/1992 | Olive ....................... 128/705 |
| 5,117,824 A | 6/1992 | Keimel et al. ......... 128/419 D |
| 5,129,392 A | 7/1992 | Bardy |
| 5,161,527 A | 11/1992 | Nappholz et al. ..... 128/419 PG |
| 5,163,427 A | 11/1992 | Keimel .................. 128/419 D |
| 5,188,105 A | 2/1993 | Keimel .................. 128/419 D |
| 5,193,535 A | 3/1993 | Bardy et al. ........... 128/419 D |
| 5,203,326 A * | 4/1993 | Collins ........................ 607/4 |
| 5,205,583 A | 4/1993 | Henseler et al. ........... 280/743 |
| 5,217,021 A | 6/1993 | Steinhaus et al. ......... 128/702 |
| 5,312,441 A | 5/1994 | Mader et al. ................ 607/5 |
| 5,342,402 A | 8/1994 | Olson et al. ................. 607/5 |
| 5,545,186 A | 8/1996 | Olson et al. ................ 607/14 |
| 5,653,740 A | 8/1997 | Degroot |
| 5,855,593 A | 1/1999 | Olson et al. ................. 607/9 |

(Continued)

FOREIGN PATENT DOCUMENTS

EP    0536873 B1    9/1997

(Continued)

Primary Examiner—George Manuel
Assistant Examiner—Nicole R. Kramer
(74) Attorney, Agent, or Firm—Michael C. Soldner; Girma Wolde-Michael

(57) ABSTRACT

An implantable medical device that includes a microprocessor that characterizes cardiac activity of a patient to enable the implantable medical device to deliver therapy in response to an identified arrhythmia event. A monitor/controller monitors the characterized cardiac activity and the delivered therapy, and controls activation of triggered overdrive pacing subsequent to the delivered therapy.

19 Claims, 11 Drawing Sheets

U.S. PATENT DOCUMENTS

| | | |
|---|---|---|
| 5,899,929 A | 5/1999 | Thompson |
| 5,913,550 A | 6/1999 | Watanuki ................... 29/603.1 |
| 5,951,593 A * | 9/1999 | Lu et al. ....................... 607/14 |
| 5,991,656 A | 11/1999 | Olson et al. ................... 607/4 |
| 6,052,620 A | 4/2000 | Gillberg et al. ................ 607/4 |
| 6,115,628 A | 9/2000 | Stadler et al. .............. 600/517 |
| 6,128,526 A | 10/2000 | Stadler et al. .............. 600/517 |
| 6,141,581 A | 10/2000 | Olson et al. ................ 600/515 |
| 6,178,350 B1 | 1/2001 | Olson et al. ................... 607/4 |
| 6,253,102 B1 * | 6/2001 | Hsu et al. ................... 600/515 |
| 6,259,947 B1 | 7/2001 | Olson et al. ................... 607/4 |
| 6,351,668 B1 | 2/2002 | Chen |
| 6,470,210 B1 * | 10/2002 | Chen et al. ................ 600/515 |
| 6,718,198 B1 * | 4/2004 | Conley et al. ............. 600/523 |
| 6,829,504 B1 * | 12/2004 | Chen et al. ................... 607/4 |

FOREIGN PATENT DOCUMENTS

| | | |
|---|---|---|
| WO | WO 92/18198 | 10/1992 |

* cited by examiner

METHOD AND APPARATUS FOR PREVENTION OF ARRHYTHMIA CLUSTERS USING OVERDRIVE PACING

FIELD OF THE INVENTION

The present invention relates generally to implantable medical devices that detect and/or treat tachyarrhythmias (rapid heart rhythms), and in particular, the present invention relates to reducing the incidence of arrhythmia clusters using heart rate/interval based adjustable overdrive pacing.

BACKGROUND OF THE INVENTION

In the medical fields of cardiology and electrophysiology, many tools are used to assess the condition and function of a patient's heart, including the observed frequency, and morphology of the PQRST complex associated with a heart cycle. Such tools include classic external ECG systems for displaying and recording the characteristic lead ECG signals from skin electrodes placed on the patient's chest and limbs, ambulatory ECG Holter monitors for continuously recording the ECG or segments thereof from a more limited set of skin electrodes for a period of time, and more recently developed completely implantable cardiac monitors or cardiac pacemakers and implantable cardioverter/defibrillators (ICDs) having the capability of recording electrogram (EGM) segments or data derived from atrial and ventricular EGMS (A-EGMs and V-EGMs) for telemetry out to an external programmer for external storage and display.

Early automatic detection systems for automatic cardioverter/defibrillators relied upon the presence or absence of electrical and mechanical heart activity (such as intramyocardial pressure, blood pressure, impedance, stroke volume or heart movement) and/or the rate of the electrocardiogram to detect hemodynamically compromising ventricular tachycardia or fibrillation.

Presently available pacemaker/cardioverter/defibrillator arrhythmia control devices employ programmable fibrillation interval ranges and tachycardia detection interval ranges, along with measurement of suddenness of onset and rate variability. For future generations of devices, numerous detection and classification systems have been proposed. Numerous patents, including U.S. Pat. No. 5,217,021 issued to Steinhaus et al., U.S. Pat. No. 5,086,772 issued to Larnard et al., U.S. Pat. No. 5,058,599 issued to Andersen and U.S. Pat. No. 5,312,441 issued to Mader et. Al., propose waveform morphology analysis systems for determining the type and origin of detected arrhythmias. Other patents, including U.S. Pat. No. 5,205,583 issued to Olson, U.S. Pat. No. 5,913,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al. propose systems for analysis of order and timing of atrial and ventricular events.

In the existing and proposed devices discussed above, one or two basic strategies are generally followed. A first strategy is to identify heart events, event intervals or event rates as they occur as indicative of the likelihood of the occurrence of specific types of arrhythmias, with each arrhythmia having a preset group of criteria that must be met as precedent to detection or classification. As cardiac events progress, criteria for identifying the various arrhythmias are all monitored simultaneously, with the first set of criteria to be met resulting in detection and diagnosis of the arrhythmia. A second strategy is to define a set of criteria for events, event intervals and event rates which is generally indicative of a group of arrhythmias, and following those criteria being met, analyzing preceding or subsequent events to determine which specific arrhythmia is present. An arrhythmia detection and classification system generally as disclosed in U.S. Pat. No. 5,342,402, issued to Olson et al., incorporated herein by reference in its entirety, uses both strategies together. In addition, numerous patents issued to Olson et al., including, for example, U.S. Pat. No. 5,545,186, U.S. Pat. No. 5,855,593, U.S. Pat. No. 5,991,656 U.S. Pat. No. 6,141,581, U.S. Pat. No. 6,178,350, U.S. Pat. No. 6,259,947, in addition to U.S. Pat. No. 6,052,620 issued to Gillberg et al., each incorporated herein by reference in their entireties, are directed to the use of a hierarchical rule based arrhythmia detection methodology based on a set of prioritized rules, each of the rules defining a plurality of criteria based upon characteristics of sensed depolarizations of heart tissue, each role being met when the criteria associated with the role are met.

In certain cases, patients utilizing implantable cardioverter/defibrillators tend to experience a number of spontaneous VT/VF episodes, or arrhythmia clusters, over a short period of time. For example, between approximately 75–90% of all VT/VF episodes occur in a form of clustering, typically having interdetection intervals less than one hour. Although the causes for the occurrence of such episodes in quick succession is unclear, myocardial ischemia, electrolyte imbalance, neurological disturbance, hormonal changes, and drugs are thought to be possible factors. While current implantable cardioverter/defibrillators treat specific, single VT/VF episodes, present implantable cardioverter/defibrillators do not attempt to detect arrhythmia clusters and to prevent the occurrence of future episodes that are associated with the detected arrhythmia cluster. Accordingly, what is needed is a method and device for automatically detecting the occurrence of arrhythmia clusters and preventing future episodes.

SUMMARY OF THE INVENTION

The present invention relates to an implantable medical device that includes a microprocessor that characterizes cardiac activity of a patient to enable the implantable medical device to deliver therapy in response to an identified arrhythmia event. A monitor/controller monitors the characterized cardiac activity and the delivered therapy, and controls activation of triggered overdrive pacing subsequent to the delivered therapy.

According to a preferred embodiment of the present invention, the monitor/controller determines whether an arrhythmia event has terminated in response to the delivered therapy, determines whether to terminate triggered overdrive pacing in response to triggered overdrive pacing being active, determines whether the arrhythmia event is associated with an arrhythmia cluster in response to triggered overdrive pacing not being active, and activates triggered overdrive pacing in response to the arrhythmia event being associated with an arrhythmia cluster and triggered overdrive pacing being appropriate.

The present invention is further directed to a method for detecting arrhythmias in an implantable medical device that includes determining whether an arrhythmia event has terminated in response to a delivered therapy, determining whether triggered overdrive pacing is active, determining whether to terminate triggered overdrive pacing in response to triggered overdrive pacing being active, determining whether the arrhythmia event is associated with an arrhythmia cluster in response to triggered overdrive pacing not being active, determining whether triggered overdrive pacing is appropriate, and delivering triggered overdrive pacing in response to the arrhythmia event being associated with an arrhythmia cluster and triggered overdrive pacing being appropriate.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

DETAILED DESCRIPTION OF THE PREFERRED EMBODIMENTS

Figure 1:
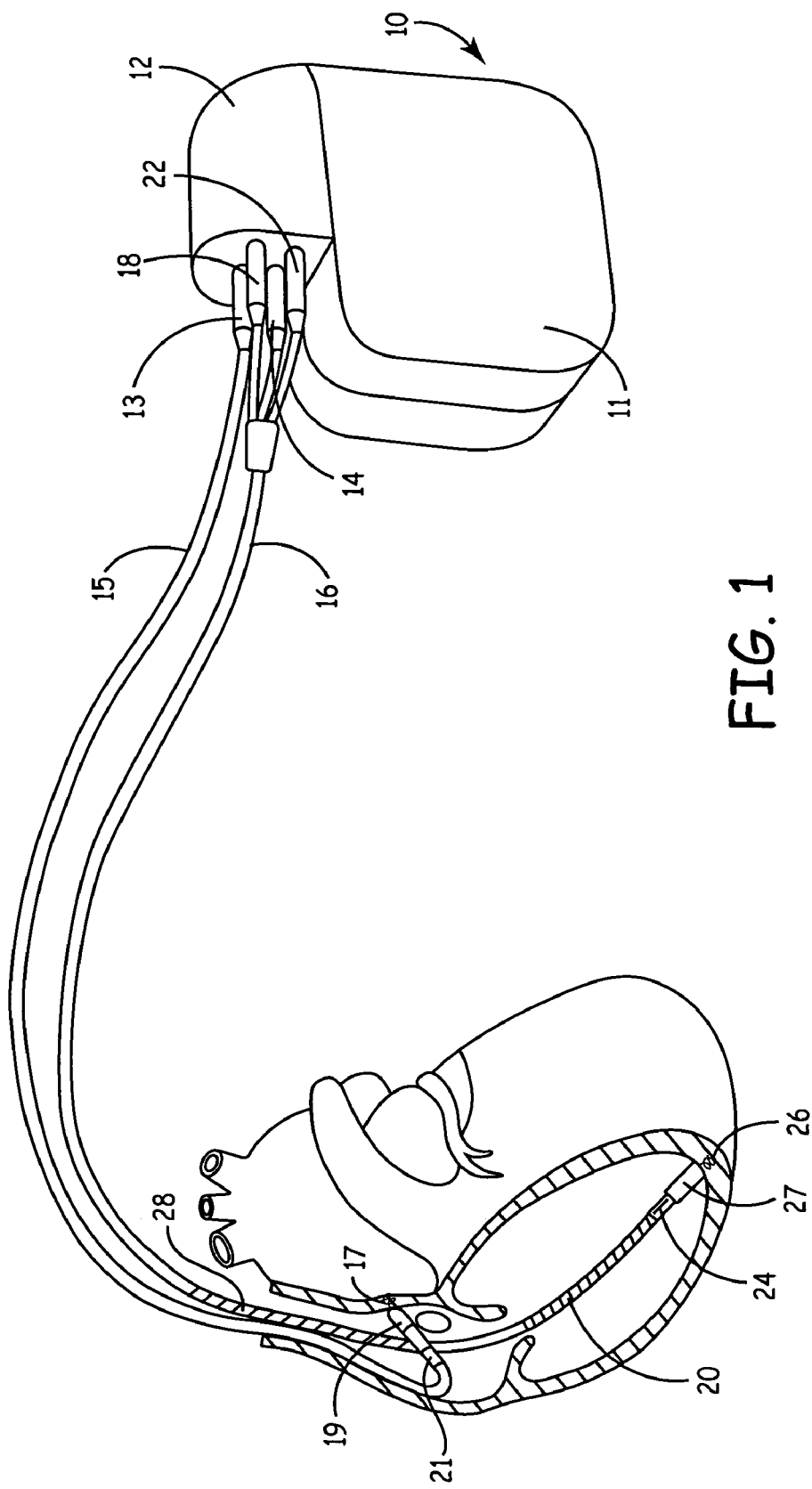
FIG. 1 is a schematic diagram of an implantable medical device for implementing a heart rhythm classification methodology for detecting tachyarrhythmias according to the present invention.

FIG. 1 is a schematic diagram of an implantable medical device for implementing a heart rhythm classification methodology for detecting tachyarrhythmias according to the present invention. As illustrated in FIG. 1, a ventricular lead of an implantable medical device 10 according to the present invention, such as a pacemaker/cardioverter/defibrillator, for example, includes an elongated insulative lead body 16, carrying four mutually insulated conductors. Located on lead body 16 are a ring electrode 24, an extendable helix electrode 26 mounted retractably within an insulative electrode head 27, and elongated coil electrodes 20 and 28. Each of the electrodes is coupled to one of the coiled conductors within the lead body 16. Electrodes 24 and 26 are employed for cardiac pacing and for sensing ventricular depolarizations. Electrodes 20 and 28 are employed in conjunction with the conductive housing 11 of the implantable medical device 10 for delivery of ventricular cardioversion and defibrillation pulses. At the proximal end of the lead body 16 are two unipolar connectors 18 and 22 which each carry a connector pin coupled to one of the coiled electrodes 20 and 28. Electrical connector 14 is an in-line bipolar connector carrying a connector ring and a connector pin, coupled to electrodes 24 and 26, respectively.

The atrial lead as illustrated is a conventional bipolar atrial pacing lead. The atrial lead includes an elongated insulative lead body 15, carrying two concentric coiled conductors, separated from one another by tubular insulative sheaths. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. At the proximal end of the lead is an in-line connector 13, which carries a connector ring and a connector pin, coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein.

Implantable medical device 10 is shown in combination with the leads, with the lead connectors 13, 14, 18 and 22 inserted into the connector block 12, which contains corresponding electrical connectors for coupling to the various connector rings and pins. Optionally, insulation of the outward facing portion of the housing 11 of the implantable medical device 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of electrodes 20 and 28.

Figure 2:
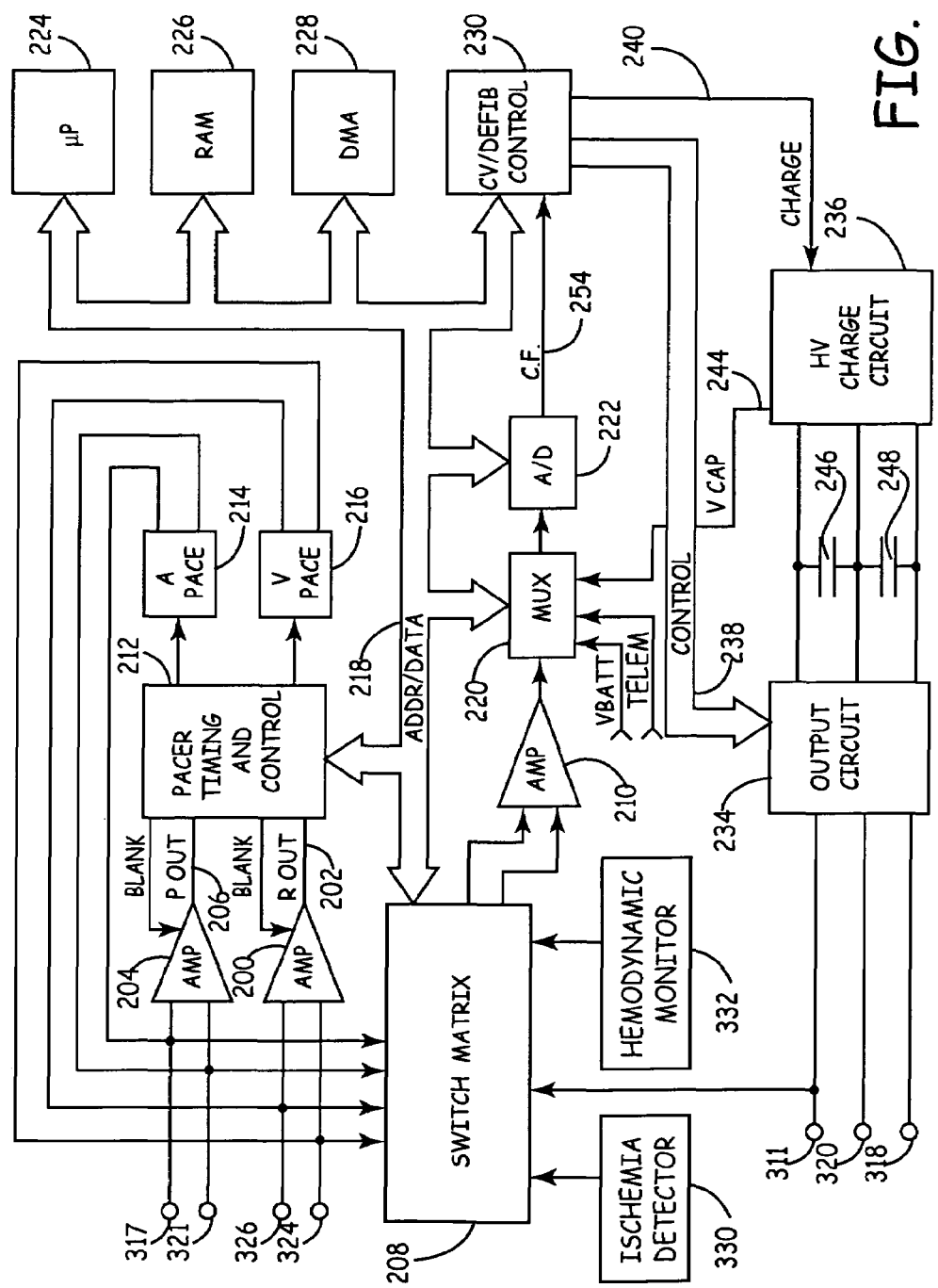
FIG. 2 is a functional schematic diagram of an implantable medical device in which the present invention may usefully be practiced.

FIG. 2 is a functional schematic diagram of an implantable medical device in which the present invention may usefully be practiced. It is understood that FIG. 2 should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, antitachycardia pacers which do not provide cardioversion or defibrillation, and devices which deliver different forms of anti-arrhythmia therapies such nerve stimulation or drug administration.

As illustrated in FIG. 1, implantable medical device 10 is provided with a lead system including electrodes, which may be as illustrated in FIG. 1. However, it is understood that alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable medical device. Electrode 320 corresponds to electrode 20 and is a defibrillation electrode located in the right ventricle. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311,318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on Rout line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art. In addition, microprocessor 224 selects whether information provided by an ischemia detector 330 and/or a hemodynamic monitor 332 is used to detect ischemia and/or blood pressure of the patient through switch matrix 208.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, P-R intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 (FIG. 4) may be configured as a plurality of re-circulating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Hess et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry that may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemakers/ cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such preset therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 2A:
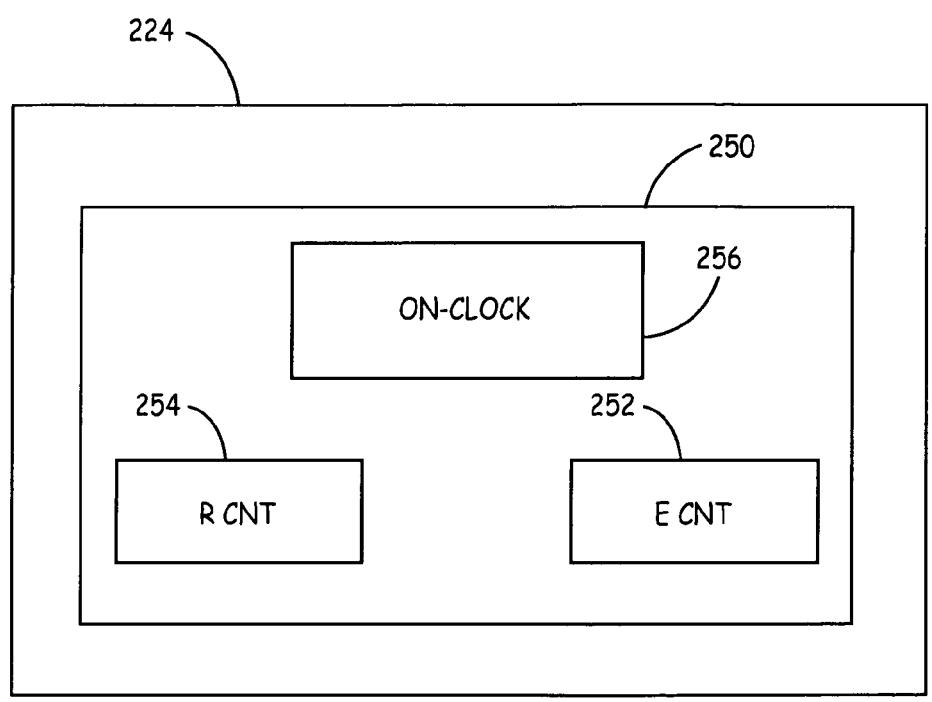
FIG. 2A is a simplified schematic diagram of a microprocessor of the implantable medical device of FIG. 2.

FIG. 2A is a simplified schematic diagram of a microprocessor of the implantable medical device of FIG. 2. As illustrated in FIG. 2A, microprocessor 224 includes a triggered overdrive pacing (TOP) monitor/controller 250 for monitoring and controlling the activation and deactivation of triggered overdrive pacing generated via pacer output circuitry 214 and 216 in accordance with the present invention. Monitor/controller 250 includes at least one event counter (ECNT) 252 for counting the number of ventricular tachycardia (VT) events, fast ventricular tachycardia (FVT) events, ventricular fibrillation (VF) events, and non-sustained ventricular tachycardia (NSVT) events that are detected, along with at least one event counter (RCNT) 254 for counting the number of events that occur during prior or current triggered overdrive pacing interventions once triggered overdrive pacing is activated, and at least one ON-clock (ON-CLK) 256, as will be described in detail below.

Figure 3:
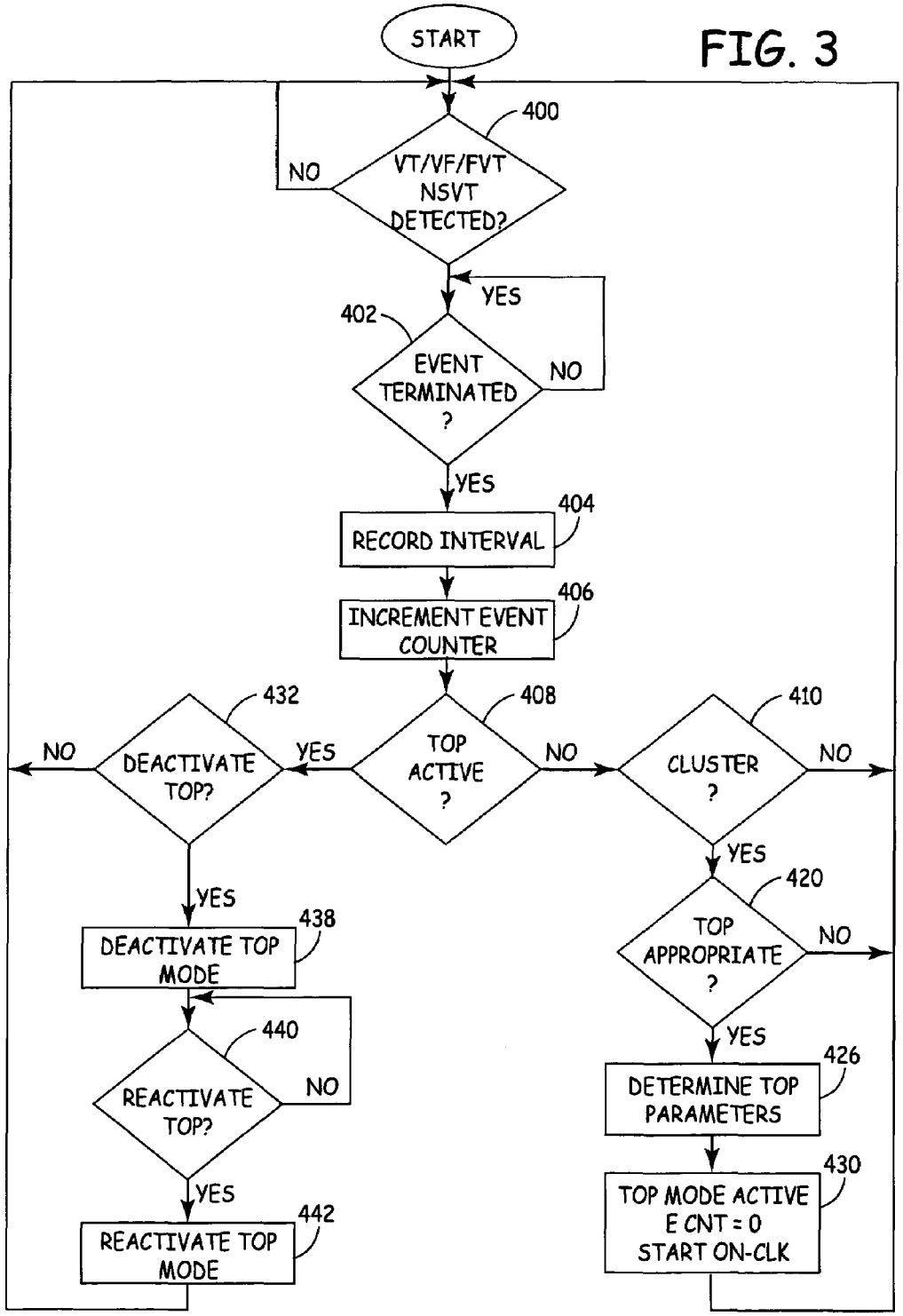
FIG. 3 is a flowchart of a method for detecting arrhythmias in an implantable medical device according to the present invention.

FIG. 3 is a flowchart of a method for detecting arrhythmias in an implantable medical device according to the present invention. As illustrated in FIGS. 2 and 3, in a method for detecting arrhythmias that reduces the incidence of arrhythmia clusters in implantable medical device 10 according to the present invention, microprocessor 224 characterizes digitized signals corresponding to cardiac activity of the patient that are received by implantable medical device 10, as described above, to recognize and classify the patient's heart rhythm employing any of the numerous signal processing methodologies known in the art. For example, microprocessor 224 detects whether a VT event, an FVT event, a VF event, or an NSVT event has occurred, Step 400. Each time a VT, FVT or VF event is detected, known techniques for addressing the event are employed by implantable medical device 10. For example, when microprocessor 224 detects a ventricular tachycardia event, implantable medical device 10 performs anti-tachy cardia pacing or shock therapy, depending on how implantable medical device 10 is programmed by the physician. When microprocessor 224 detects a ventricular fibrillation event, implantable medical device 10 performs shock treatment. When microprocessor 224 detects a fast ventricular tachycardia event, implantable medical device performs either shock therapy or anti-tachycardia pacing therapy, depending on how the device 10 is programmed by the physician. Since non-sustained ventricular tachycardia events, by definition, self-terminate, such events do not require termination techniques to be performed by implantable medical device 10.

Monitor/controller 250 continues to monitor the results of the classification of events and resulting therapy delivered, so that once either there is termination of a detected VT, FVT or VF event following a corresponding termination technique, or, in the case of self termination of a non-sustained ventricular tachycardia (NSVT) event, once the non-sustained ventricular tachycardia event has terminated, Step 402, monitor/controller 250 records an inter-detection interval between the detected event and a previously detected event, Step 404, increments event counter 252, Step 406, and determines whether triggered overdrive pacing (TOP) is active, i.e., whether triggered overdrive pacing is currently being delivered, Step 408. If triggered overdrive pacing is inactive, i.e., not currently being delivered in Step 408, a determination is then made as to whether the current detected event is associated with an arrhythmia cluster, Step 410.

Figure 4:
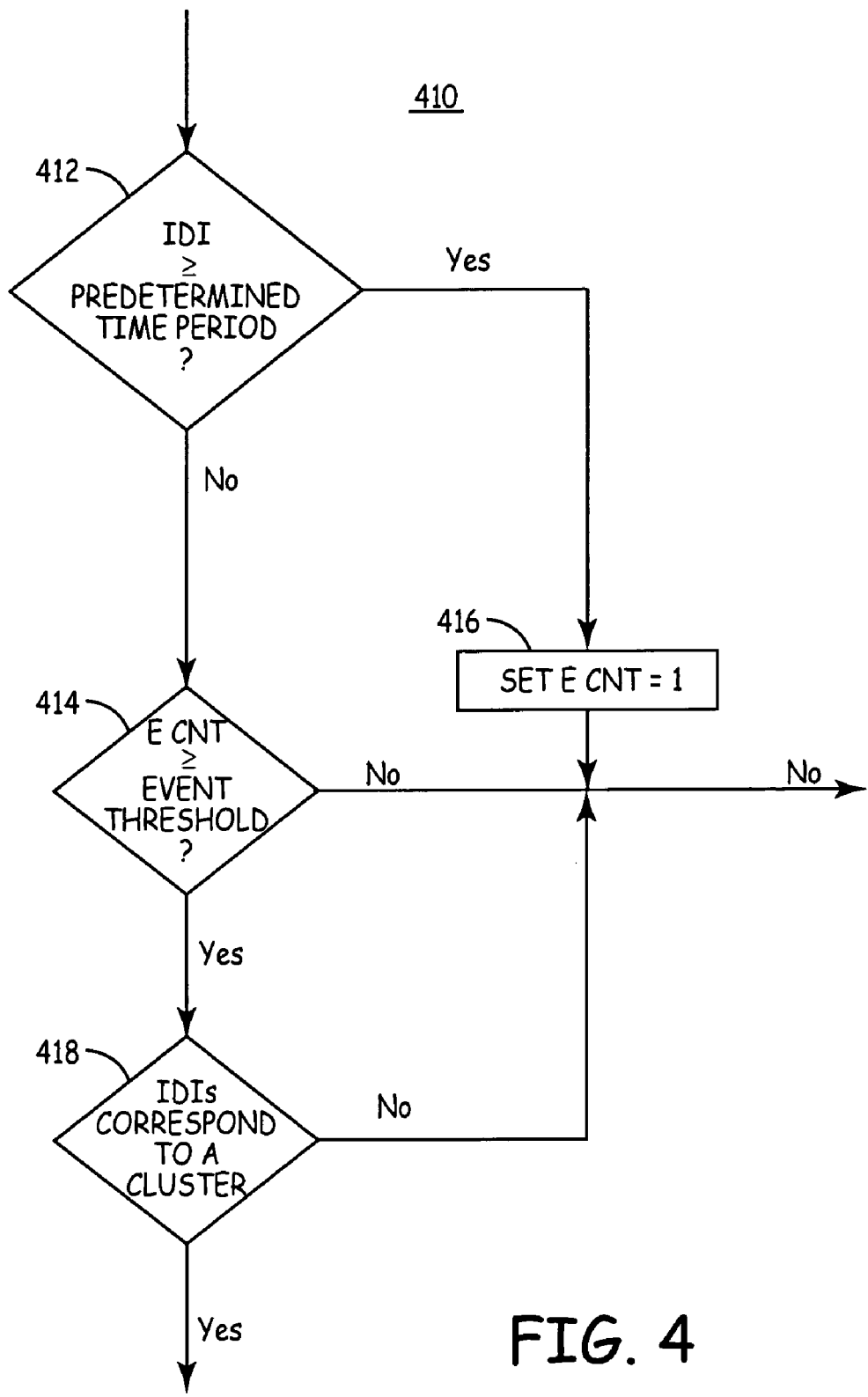
FIG. 4 is a flowchart of a method for determining whether a detected event is associated with an arrhythmia cluster in a method for detecting arrhythmias in an implantable medical device according to a preferred embodiment of the present invention.

FIG. 4 is a flowchart of a method for determining whether a detected event is associated with an arrhythmia cluster in a method for detecting arrhythmias in an implantable medical device according to a preferred embodiment of the present invention. As illustrated in FIG. 4, according to a preferred embodiment of the present invention, when determining whether the current detected event is associated with an arrhythmia cluster, Step 410 of FIG. 3, monitor/controller 250 determines whether the inter-detection interval (IDI) associated with the current detected event is greater than or equal to a predetermined time period, Step 412. If the inter-detection interval is greater than or equal to the predetermined time period, indicating that an arrhythmia cluster is not currently present, or the patient has just come out of an arrhythmia cluster, event counter 252 is set equal to one, Step 416, and the process waits for a next detected event to occur in Step 400. On the other hand, if the inter-detection interval is not greater than the predetermined time period, a determination is made as to whether a predetermined number of events associated with identifying an arrhythmia cluster have been detected by determining whether event counter 252 is greater than or equal to a predetermined event threshold, Step 414.

According to the present invention, an arrhythmia cluster is generally identified as occurring when a number of detected events occur close in relative close proximity to each other in time. For example, according to a preferred embodiment of the present invention, a number of detected events are determined to occur close in relative close proximity to each other in time, signaling the occurrence of an arrhythmia cluster, when inter-detection intervals associated with a predetermined number of events corresponds to an arrhythmia cluster, as will be described below. According to an alternate embodiment of the present invention, an arrhythmia cluster is generally identified as including a predetermined number of events occurring in a predetermined time period, which, according to a preferred embodiment of the present invention for example includes four events occurring within a 24-hour period, as described below.

Figure 5:
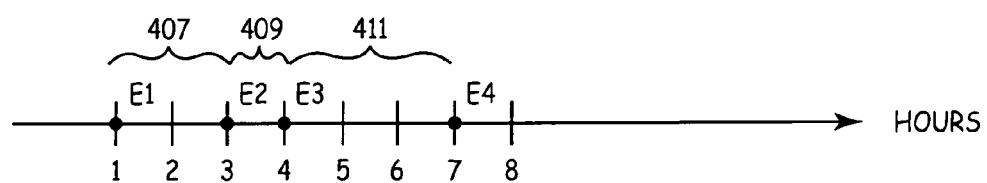
FIGS. 5 and 6 are simplified flow chart diagrams illustrating measurement of an inter-detection interval between detected events according to the present invention.
Figure 6:
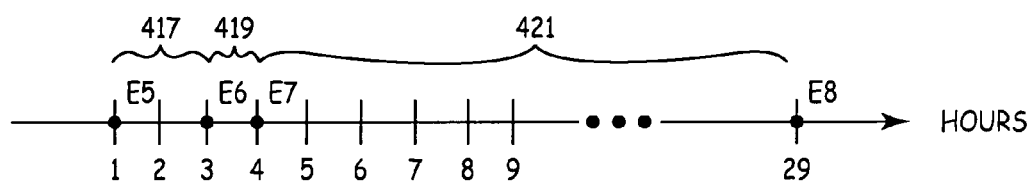

FIGS. 5 and 6 are simplified flow chart diagrams illustrating measurement of an inter-detection interval between detected events according to the present invention. As illustrated in FIGS. 3, 4 and 5, upon termination of an event, Step 402, monitor/controller 250 records an inter-detection interval between a current terminated event and a previously terminated event in Step 404, and increments event counter 252, Step 406. Monitor/controller 250 then determines whether triggered overdrive pacing is active or is currently being delivered, Step 408, and if triggered overdrive pacing is not currently being delivered, determines whether the current terminated event is associated with an arrhythmia cluster, Step 410. In particular, upon termination of an event E1 as a result of specific termination techniques or as a result of self-termination, as described above, monitor/controller 250 records the inter-detection interval between the current event E1 associated with that terminated event and a previously terminated event. However, since, in the example of FIG. 5 there is no previously terminated event for E1, no inter-detection interval is recorded. Although the inter-detection interval associated with event E1 is not greater than or equal to the predetermined time period, NO in Step 412, since event counter 252 is less than the event threshold, and therefore the predetermined number of events (i.e., 4) have not been detected, NO in Step 414, event E1 is determined not to be associated with an arrhythmia cluster, NO in Step 410. As a result, the process waits for a next event E2 to occur in Step 400.

Upon termination of the next detected event E2, an inter-detection interval 407 between the current event E2 and previous terminated event E1 is recorded, Step 404, and event counter 252 is incremented, Step 406. Assuming that the predetermined time period is 24 hours, for example, although inter-detection interval 407 associated with event E2 is not greater than or equal to the predetermined time period, NO in Step 412, since event counter 252 is less than the event threshold, and therefore the predetermined number of events have not been detected, NO in Step 414, event E2 is determined not to be associated with an arrhythmia cluster, NO in Step 410. As a result, the process waits for a next event E3 to occur in Step 400.

While the predetermined event threshold described above for Step 414 in this preferred embodiment of the present invention is set equal to four and the predetermined time period for Step 412 is set equal to 24 hours, it is understood that the event threshold and the predetermined time period are not intended to be limited to the use of these values, but rather the present invention could utilize any number of events for the event threshold in combination with any desired time period that is determined to most accurately identify an arrhythmia cluster.

Upon termination of the next detected event E3, an inter-detection interval 409 between the current event E3 and the previous terminated event E2 is recorded, Step 404, and event counter 252 is incremented, Step 406. Although inter-detection interval 409 associated with event E3 is not greater than or equal to the predetermined time period, NO in Step 412, since event counter 252 is less than the event threshold, and therefore the predetermined number of events have not been detected, NO in Step 414, event E3 is determined not to be associated with an arrhythmia cluster, NO in Step 410. As a result, the process waits for a next event E4 to occur in Step 400.

Upon termination of the next detected event E4, an inter-detection interval 411 between the current event E4 and the previous terminated event E3 is recorded, Step 404, and event counter 252 is incremented, Step 406. Assuming, by way of example, that inter-detection intervals 407, 409 and 411 are, as shown in FIG. 5, approximately equal to 2 hours, 1 hour and 3 hours, respectively, once inter-detection interval 411 has been recorded, Step 404, and event counter 252 has been incremented upon termination of the fourth event E4, Step 406, inter-detection interval 411 associated with events E4 will be determined to be not greater than or equal to the predetermined time period, NO in Step 412. However, since event counter 252 is now equal to four, event counter 252 will be determined to be greater than or equal to the predetermined event threshold, indicating that the predetermined number of events have been detected, YES in Step 414. Once the predetermined number of events have been detected in Step 414, a determination is made as to whether inter-detection intervals associated with the predetermined number of events corresponds to a cluster, Step 418, described below.

In particular, using the events detected as set forth in FIG. 5, once both the total inter-detection interval is less than the predetermined time period, No in Step 412, and event counter 252 is greater than or equal to the predetermined event threshold, indicating that the predetermined number of events have been detected, Yes in Step 414, monitor/controller 250 determines whether inter-detection intervals 407, 409 and 413 associated with the predetermined number of arrhythmia events E1–E4 corresponds to an arrhythmia cluster, Step 418. For example, according to a preferred embodiment of the present invention, the determination as to whether inter-detection intervals 407, 409 and 413 associated with the predetermined number of arrhythmia events E1–E4 corresponds to an arrhythmia cluster, Step 418, includes determining whether a median of the inter-detection intervals between current detected events, i.e., intervals 407, 409 and 411, is less than or equal to a predetermined median threshold, Step 418. If the median of the inter-detection intervals 407, 409, and 411 is greater than the predetermined median threshold, the current detected event E4 is determined not to be associated with an arrhythmia cluster, NO in Step 418, and the process waits for a next detected event to occur in Step 400. However, if the median of the inter-detection intervals 407, 409 and 411 is less than or equal to the predetermined median threshold, the current detected event E4 is determined to be associated with an arrhythmia cluster, YES in Step 418. Once the current detected event is determined to be associated with an arrhythmia cluster, a determination is made as to whether triggered overdrive pacing is appropriate for the current detected event, Step 420 (FIG. 3).

As a result, the alternative embodiment of the present invention determines whether an event is associated with an arrhythmia cluster in Step 410 by looking at the number of events occurring in a predetermined time period, the inter-detection interval between events, and a median of intervals between events. As a result, according to the alternate embodiment of the present invention, if the inter-detection interval is greater than or equal to the predetermined time period, event counter 252 is less than the predetermined event threshold, or the median of the intervals is greater than the predetermined median threshold, the current detected event is determined not to be associated with an arrhythmia cluster, NO in Step 410, and the process waits for a next event to occur in Step 400. On the other hand, if the predetermined number of events have been detected within the predetermined time period and the median of the intervals is less than or equal to the predetermined median threshold, the current detected event is determined to be associated with an arrhythmia cluster, YES in Step 410.

The predetermined median threshold is programmable by the physician in accordance to the specific needs of the patient. According to a preferred embodiment of the present invention, the predetermined median threshold is programmed as being one hour, although the present invention is not intended to be limited to one hour, but rather includes the use of any programmed predetermined median threshold. In addition, it is understood that while the determination of whether an event is associated with an arrhythmia cluster has been described in terms of determining whether a median interval is less than or equal to a median threshold, other methods could be utilized to determine if the event is associated with an arrhythmia cluster in accordance with the present invention. For example, rather than determining whether a median of the intervals is less than or equal to a median threshold, Step 418 according to an alternate embodiment of the present invention, the determination of Step 418 includes determining whether a mean of the intervals is less than or equal to a mean threshold. In yet another alternate embodiment of the present invention, Step 418 includes determining whether the sum of the inter-detection intervals is less than a predetermined inter-detection interval threshold, which is equivalent to determining a mean without the need for dividing.

As illustrated in FIGS. 3, 4 and 6, in the same way as described above in reference to intervals 407, 409 and 411 in FIG. 5, upon termination of an event, Step 402, monitor/controller 250 records an inter-detection interval between a current terminated event and a previously terminated event in Step 404, and increments event counter 252. Monitor/controller 250 then determines whether triggered overdrive pacing is currently being delivered, Step 408, and if triggered overdrive pacing is not currently being delivered, determines whether the current terminated event is associated with an arrhythmia cluster, Step 410. In particular, upon termination of an event E5 as a result of specific termination techniques or as a result of self-termination, as described above, monitor/controller 250 records the inter-detection interval between the current event E5 associated with that terminated event and a previously terminated event. However, since, in the example of FIG. 6 there is no previously terminated event for E5, no inter-detection interval is recorded. Although the inter-detection interval associated with event E5 is not greater than or equal to the predetermined time period, NO in Step 412, since event counter 252 is less than the event threshold, and therefore the predetermined number of events have not been detected, NO in Step 414, event E5 is determined not to be associated with an arrhythmia cluster, NO in Step 410. As a result, the process waits for a next event E6 to occur in Step 400.

Upon termination of the next detected event E6, an inter-detection interval 417 between the current event E6 and previous terminated event E5 is recorded, Step 404, and event counter 252 is incremented, Step 406. Although inter-detection interval 417 associated with event E6 is not greater than or equal to the predetermined time period, NO in Step 412, since event counter 252 is less than the event threshold and therefore the predetermined number of events have not been detected, NO in Step 414, event E6 is determined not to be associated with an arrhythmia cluster, NO in Step 410. As a result, the process waits for a next event E7 to occur in Step 400.

Upon termination of the next detected event, E7 an inter-detection interval 419 between the current detected event E7 and the previous terminated detected event E6 is recorded, Step 404, and event counter 252 is incremented, Step 406. Although inter-detection interval 419 associated with event E7 is not greater than or equal to the predetermined time period, NO in Step 412, since event counter 252 is less than the event threshold and therefore the predetermined number of events have not been detected, NO in Step 414, event E7 is also determined not to be associated with an arrhythmia cluster, NO in Step 410, and the process waits for a next event E8 to occur in Step 400.

Assuming by way of example, that inter-detection intervals 417 and 419 are approximately equal to 2 hours and 1 hour, respectively, once an inter-detection interval 421 corresponding to termination of the next detected event E8 and the previous terminated event E7 has been recorded, Step 404, and event counter 252 has been incremented, Step 406, and assuming further that inter-detection interval 423 is equal to 25 hours, for example, indicating that the patient has come out of an arrhythmia cluster, inter-detection interval 421 associated with event E8 will be determined to be greater than or equal to the predetermined time period, YES in Step 412. The increment counter will then be set equal to one and event E8 will be determined not to be associated with an arrhythmia cluster, NO in Step 410, and the process waits for a next event E9 to occur in Step 400, and so forth. In this way, the present invention accounts for situations when the patient has likely come out of an arrhythmia cluster, and reinitiates the process once such a situation occurs.

Figure 4A:
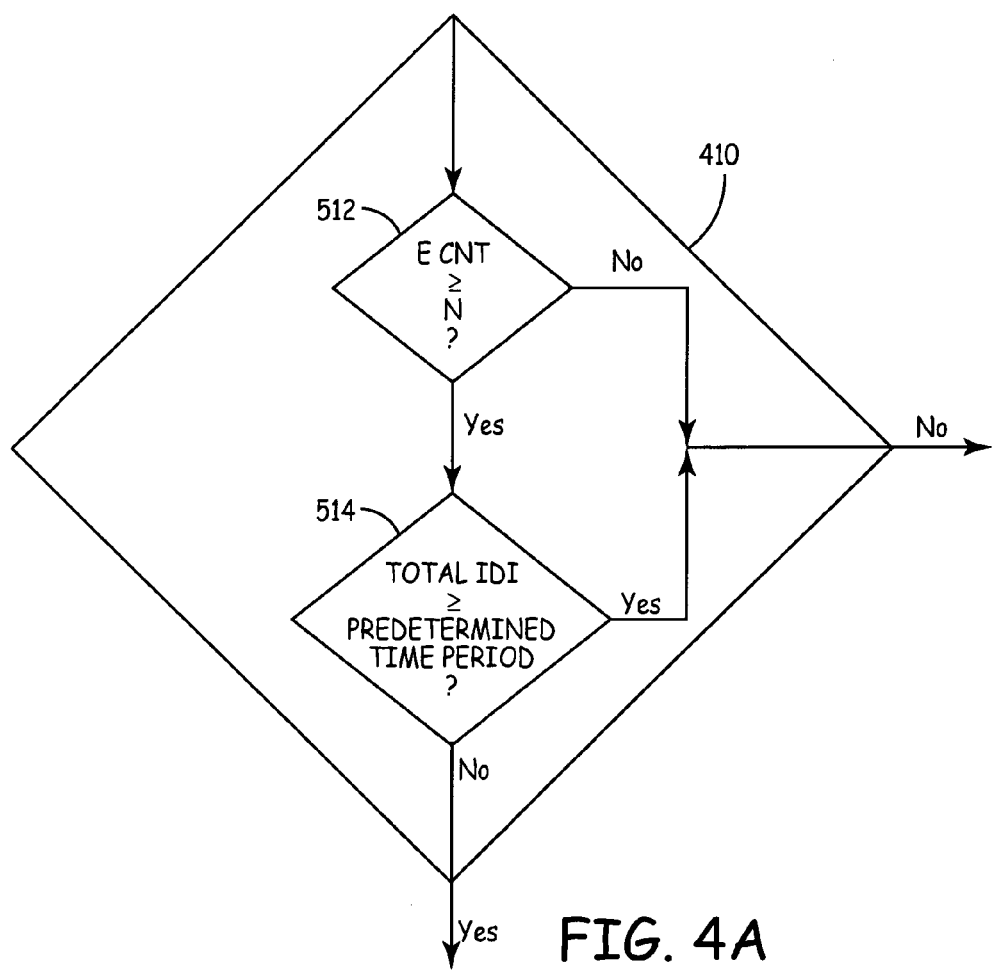
FIG. 4A is a flowchart of a method for determining whether a detected event is associated with an arrhythmia cluster in a method for detecting arrhythmias in an implantable medical device according to an alternate embodiment of the present invention.

FIG. 4A is a flowchart of a method for determining whether a detected event is associated with an arrhythmia cluster in a method for detecting arrhythmias in an implantable medical device according to an alternate embodiment of the present invention. According to the alternate embodiment of the present invention, an arrhythmia cluster is generally identified as including a predetermined number of events N occurring in a predetermined time period, which, according to a preferred embodiment of the present invention includes four events occurring within a 24-hour period, as described below. However, it is understood that the event threshold and the predetermined time period are not intended to be limited to the use of these values, but rather the present invention could utilize any number of events for the event threshold in combination with any desired time period that is determined to most accurately identify an arrhythmia cluster.

As illustrated in FIG. 4A, the alternate embodiment of the present invention for determining whether a detected event is associated with an arrhythmia cluster includes determining whether the sum of the prior N−1 inter-detection intervals associated with the predetermined number of events N is less than or equal to the predetermined time period, Steps 512 and 514. In particular, as illustrated in FIGS. 3, 4A and 5, upon termination of an event, Step 402, monitor/controller 250 records an inter-detection interval between a current terminated event and a previously terminated event in Step 404, and increments event counter 252, Step 406. Monitor/controller 250 then determines whether triggered overdrive pacing is active or is currently being delivered, Step 408, and if triggered overdrive pacing is not currently being delivered, determines whether the current terminated event is associated with an arrhythmia cluster, Step 410. In particular, upon termination of an event E1 as a result of specific termination techniques or as a result of self-termination, as described above, monitor/controller 250 records the inter-detection interval between the current event E1 associated with that terminated event and a previously terminated event. However, since, in the example of FIG. 5 there is no previously terminated event for E1, no inter-detection interval is recorded. If triggered overdrive pacing is not active in Step 408, a determination is made as to whether event counter 252 is greater than or equal to the predetermined number of events, i.e., four events for example, Step 512. Since event counter 252 is not greater than or equal to the predetermined number of events, event E1 is determined not to be associated with an arrhythmia cluster, NO in Step 410. As a result, the process waits for a next event E2 to occur in Step 400.

Upon termination of the next detected event E2, inter-detection interval 407 between the current event E2 and previous terminated event E1 is recorded, Step 404, and event counter 252 is incremented, Step 405. If triggered overdrive pacing is not active in Step 408, a determination is made as to whether event counter 252 is greater than or equal to the predetermined number of events, Step 512. Since event counter 252 is not greater than or equal to the predetermined number of events, event E2 is determined not to be associated with an arrhythmia cluster, NO in Step 410. As a result, the process waits for a next event E3 to occur in Step 400.

Upon termination of the next detected event E3, inter-detection interval 409 between the current event E3 and previous terminated event E2 is recorded, Step 404, and event counter 252 is incremented, Step 406. If triggered overdrive pacing is not active in Step 408, a determination is made as to whether event counter 252 is greater than or equal to the predetermined number of events, Step 512. Since event counter 252 is not greater than or equal to the predetermined number of events, event E3 is determined not to be associated with an arrhythmia cluster, NO in Step 410. As a result, the process waits for a next event E4 to occur in Step 400.

Upon termination of the next detected event E4, inter-detection interval 411 between the current event E4 and previous terminated event E3 is recorded, Step 404, and event counter 252 is incremented, Step 406. If triggered overdrive pacing is not active in Step 408, a determination is made as to whether event counter 252 is greater than or equal to the predetermined number of events, Step 512. Since event E4 is the fourth event, event counter 252 will be determined to be greater than or equal to the predetermined number of events N in Step 512. Once the predetermined number of events have been detected, a determination is made as to whether the sum of the last N−1 (i.e., 3) inter-detection intervals 407–411 is greater than or equal to the predetermined time period, i.e., 24 hours, in Step 514. If the sum of the last N−1 inter-detection intervals 407–411 is greater than or equal to the predetermined time period, YES in Step 514, event E4 is determined not to be associated with an arrhythmia cluster, NO in Step 410. As a result, the process waits for a next event to occur in Step 400.

However, if the sum of the last N−1 inter-detection intervals 407–411 is not greater than or equal to the predetermined time period, NO in Step 514, event E4 is determined to be associated with an arrhythmia cluster, YES in Step 410.

Figure 7:
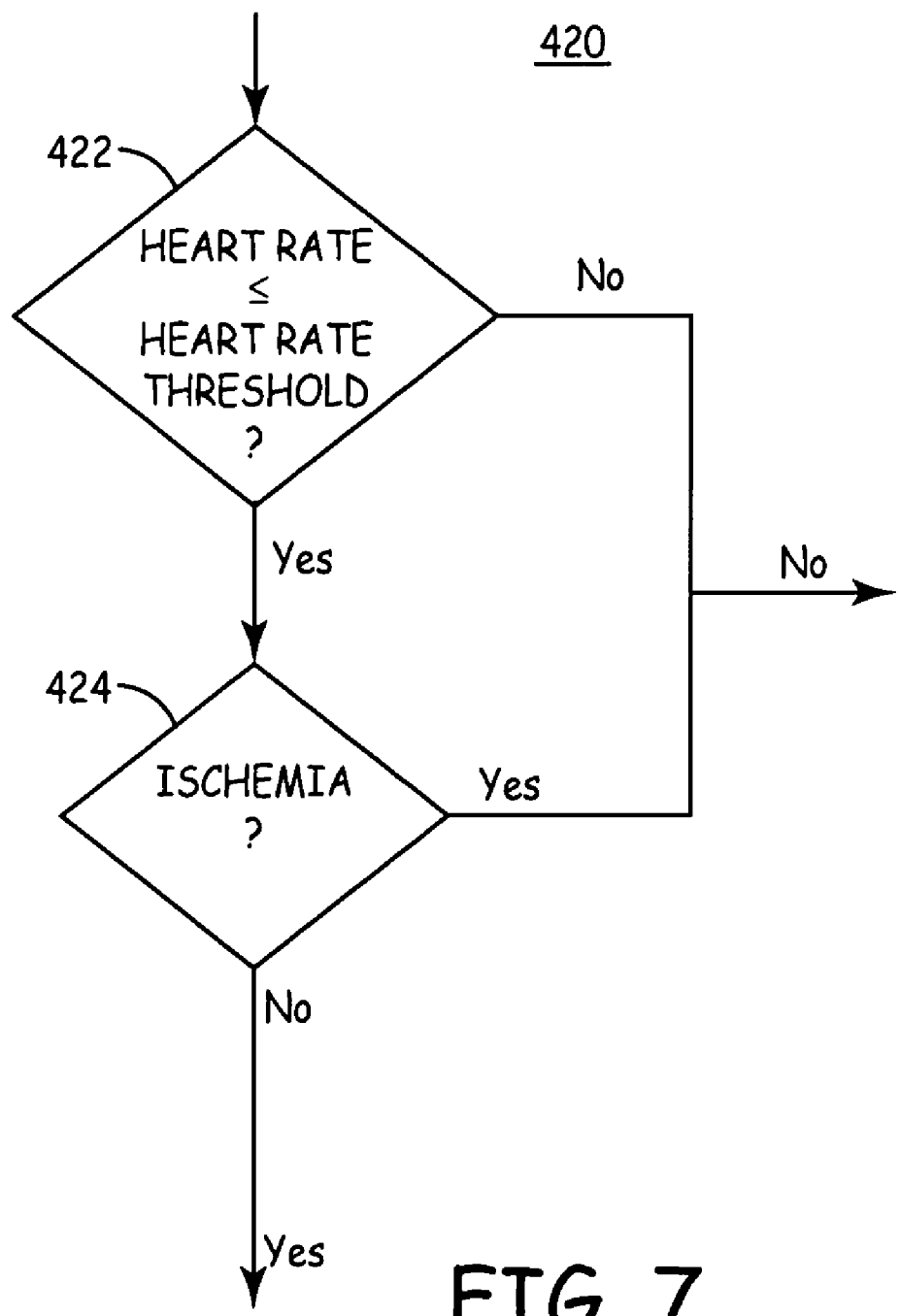
FIG. 7 is a flowchart of a method for determining whether triggered overdrive pacing is appropriate in a method for detecting arrhythmias, according to the present invention.

FIG. 7 is a flowchart of a method for determining whether triggered overdrive pacing is appropriate in a method for detecting arrhythmias, according to the present invention. As illustrated in FIG. 3, according to a preferred embodiment of the present invention, once an arrhythmia event is determined to be associated with an arrhythmia cluster, YES in Step 410, a determination is made as to whether triggered overdrive pacing is appropriate for the arrhythmia event, Step 420. If triggered overdrive pacing is determined not to be appropriate for the event, the process waits for a next event to occur in Step 400. However, if triggered overdrive pacing is determined to be appropriate for the event, monitor/controller 250 determines triggered overdrive pacing parameters, Step 426, as described below.

As illustrated in FIG. 7, the determination of whether triggered overdrive pacing is appropriate for the event in Step 420 includes, for example, determining whether a sensed heart rate is less than a first heart rate threshold, Step 422. The specific value utilized for the first heart rate threshold corresponds to a physician-determined rate above which it is undesirable to pace a given patient under any circumstances. For example, according to a preferred embodiment of the present invention, the first heart rate threshold is set as 100 beats per minute. However, it is understood that the present invention is not intended to be limited to having a first heart rate threshold equal to 100 beats per minute, but rather is intended to include any value associated with identifying tachycardia events as appropriate for each patient. For example, in certain cases it may be desirable that the patient's heart rate be allowed to reach a maximum rate that is less than 100 beats per minute, such as 90 beats per minute, for example. In addition, according to an alternate preferred embodiment of the present invention, the heart rate threshold could be computed as a percentage of the patient' resting heart rate, such as a percentage of the patient' heart rate measured during sleep, such as 120% or 125% for example, with the percentage chosen being a matter of design choice that is determined to be appropriate for the individual patient.

If the heart rate is less than the first heart rate threshold, i.e., the event does not correspond to a tachycardia event, YES in Step 422, a determination is made as to whether there is ischemia present, Step 424. According to a preferred embodiment of the present invention, the determination as to whether ischemia is present is made based on repolarization segments of an electrocardiogram, generated from data sensed at electrodes 326 and 324, for example. However, it is understood that the determination as to whether ischemia is present can be performed using any known ischemia detection methodologies, such as those disclosed for example, in U.S. Pat. Nos. 6,128,526 and 6,115,628, both issued to Stadler et al. and commonly assigned to Medtronic, Inc.

As illustrated in FIGS. 3 and 7, if the heart rate is determined to be greater than the first heart rate threshold in Step 422, or if the heart rate is determined to be less than the first predetermined threshold in Step 422 but ischemia is determined to be present in Step 424, ischemia and heart rate criteria are not met, NO in Step 420, and the process waits for a next event to occur in Step 400. On the other hand, if the heart rate is determined to be less than the first heart rate threshold in Step 422 and ischemia is determined not to be present in Step 424, i.e., ischemia and heart rate criteria are met, YES in Step 420, monitor/controller 250 determines triggered overdrive pacing parameters, Step 426.

Figure 8:
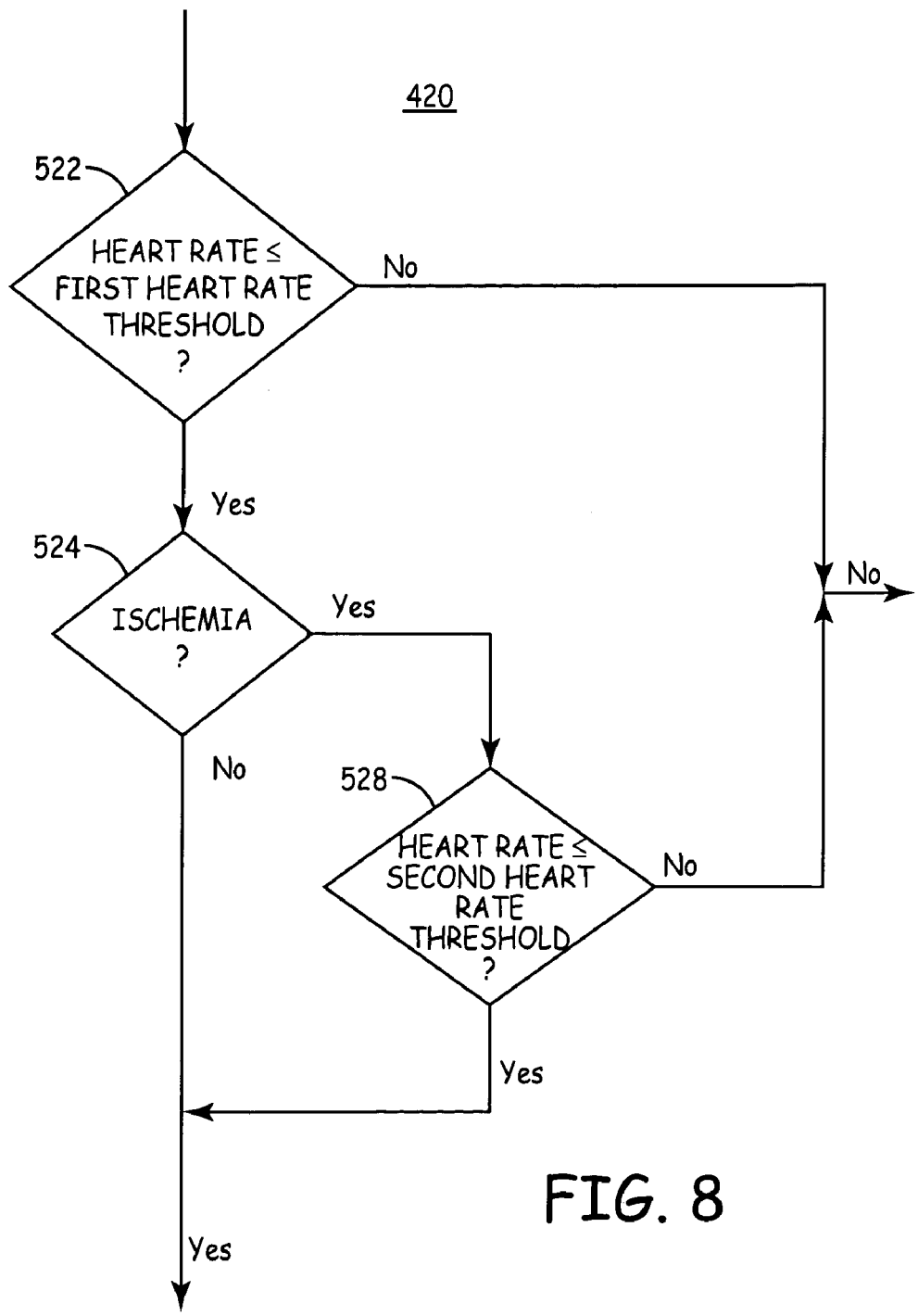
FIG. 8 is a flowchart of a method for determining whether triggered overdrive pacing is appropriate, according to an alternate embodiment of the present invention.

FIG. 8 is a flowchart of a method for determining whether triggered overdrive pacing is appropriate, according to an alternate embodiment of the present invention. In an alternative embodiment according to the present invention, the determination performed in Step 420 as to whether triggered overdrive pacing is appropriate for the current detected event includes determining whether a sensed heart rate is less than a first heart rate threshold, Step 522, and determining whether ischemia is present, Step 524, as described above in reference to FIG. 7, and therefore the description of Steps 522 and 524 of FIG. 8 is omitted for the sake of brevity. However, according to the alternate embodiment of the present invention illustrated in FIG. 8, in order to provide a second check so that triggered overdrive pacing is not completely ruled out for every instance when ischemia is present, a determination is made, in response to the sensed heart rate being less than the first heart rate threshold, YES in Step 522, and ischemia being present, YES in Step 524, as to whether the sensed heart rate is less than a second heart rate threshold, Step 528. For example, if the patient is ischemic, YES in Step 524, at a relatively moderate heart rate, say 75 beats per minute, for example, and the second heart rate threshold is set at 80 beats per minute so that the heart rate is less than the second heart rate threshold, YES in Step 528, the present invention enables triggered overdrive pacing to be activated despite the presence of moderate ischemia.

According to the present invention, while the specific value utilized for the second heart rate threshold is described above as being 80 beats per minute, it is understood that the second heart rate threshold of the present invention is not intended to be limited to that value, but rather is a design choice specific to the needs of the individual patient. In addition, according to an alternate preferred embodiment of the present invention, the second heart rate threshold is computed as a percentage of the patient' resting heart rate, such as a percentage of the patient's heart rate measured during sleep, and that is less than the percentage utilized for the first heart rate threshold, such as 105% or 110% for example, with the percentage chosen being a matter of design choice that is determined to be appropriate for the individual patient.

In this way, although it is typically not desirable to activate triggered overdrive pacing when ischemia is present, Step 528 of the present invention allows triggered overdrive pacing to be conservatively activated in certain limited instances despite the presence of ischemia.

Similar to the preferred embodiment of the present invention described in reference to FIG. 7, according to the alternate preferred embodiment of the present invention shown in FIG. 8, if the heart rate is determined to be greater than the first heart rate threshold, NO in Step 522, or if the heart rate is determined to be less than the first predetermined threshold, YES in Step 522, and both ischemia is determined to be present, YES in Step 524 and the heart rate is determined to be greater than the second heart rate threshold, NO in Step 528, ischemia and heart rate criteria are not met, NO in Step 420, and the process waits for a next event to occur in Step 400. On the other hand, if one of the heart rate is determined to be less than the first heart rate threshold, YES in Step 522 and ischemia is determined not to be present, NO in Step 524, or the heart rate is determined to be less than the first heart rate threshold, YES in Step 522, ischemia is determined to be present, YES in step 524, and the heart rate is determined to be less than the second heart rate threshold, YES in Step 528, i.e., ischemia and heart rate criteria are met, YES in Step 420, monitor/controller 250 then determines triggered overdrive pacing parameters, Step 426 (FIG. 3).

Figure 9:
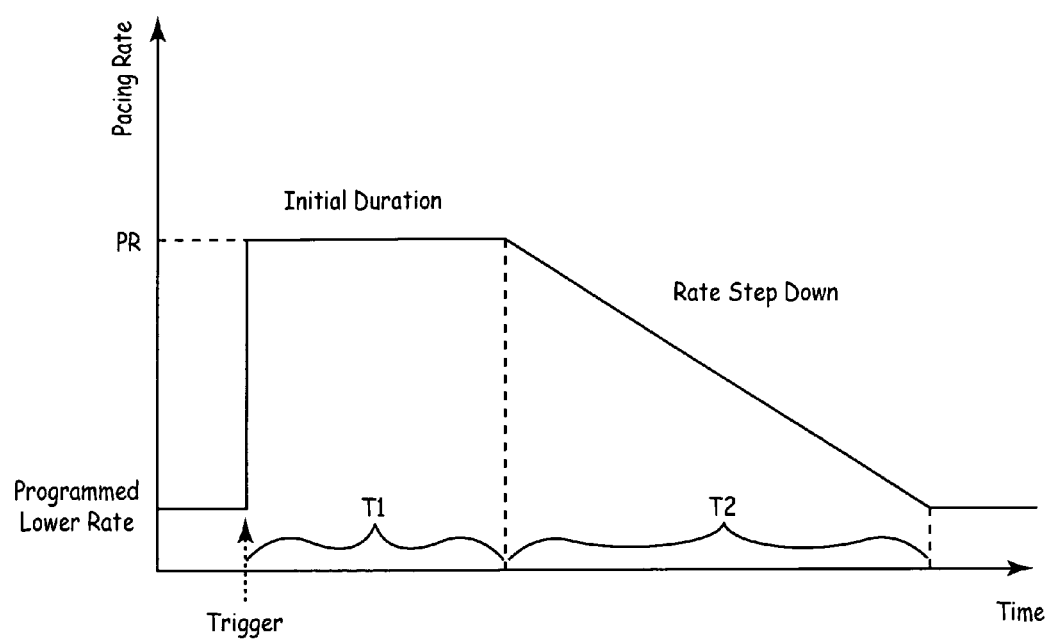
FIG. 9 is a graphical representation of delivery of overdrive pacing therapy in an implantable medical device.

FIG. 9 is a graphical representation of delivery of overdrive pacing therapy in an implantable medical device. As illustrated in FIG. 9, during triggered overdrive pacing according to the present invention, pacing of the patient is performed at a preset triggered overdrive pacing rate, PR, for a preset duration, T1, after which the triggered overdrive pacing rate is ramped off during a preset step down period, T2. According to the present invention, the determination of the triggered overdrive pacing parameters in Step 426 includes dynamically adjusting the triggered overdrive pacing rate PR based on a percentage of the existing measured heart rate of the patient. For example, according to a preferred embodiment of the present invention, the triggered overdrive pacing rate PR is adjusted to be equal to a predefined percentage of the patient's heart rate. This predefined percentage is programmable and is merely a design choice specific to individual patient's needs. For example, according to the present invention, it has been determined that the triggered overdrive pacing rate corresponds to a value between 120% and 140%, such as 125% for example. However, the present invention is not intended to be limited to this range of heart rate percentages.

According to an alternate embodiment of the present invention, the triggered overdrive pacing rate PR is dynamically adjusted based on prior success of the triggered overdrive pacing. In addition, according to yet another preferred embodiment of the present invention the triggered overdrive pacing rate PR is dynamically adjusted based on hemodynamics of the patient.

In addition to the triggered overdrive pacing rate PR, the determination of the triggered overdrive pacing parameters in Step 426 includes determining the triggered overdrive pacing duration T1. For example, duration T1 is programmable at a preset time period, such as between 2–4 hours, depending upon the specific requirements of the individual patient. According to a preferred embodiment of the present invention, the duration T1 is preset as being equal to 4 hours, however, it is understood that any time period may be utilized and is a matter of design choice. In addition, according to an alternate preferred embodiment, the duration T1 is automatically adjusted based on prior triggered overdrive pacing success, or based on prior triggered overdrive pacing success or presence of events during or immediately following the step down period T2. In yet another alternate embodiment of the present invention the duration T1 is determined as a percentage of the inter-detection intervals associated with the events used in Step 418 of FIG. 4A, such as the median interval, for example, selected such that the triggered overdrive pacing remains on for a period of time longer than the inter-detection interval.

In the same way, the determination of the triggered overdrive pacing parameters in Step 426 includes determining the step down period T2. For example, according to the present invention the step down period is calculated as a fraction of the duration T1, i.e., how long the triggered overdrive pacing is on, so that the longer the triggered overdrive pacing is on, or the greater the duration T1, the greater the step down period T2. For example, according to a preferred embodiment of the present invention, the step down period T2 is calculated as being 25% of the duration T1, so that if the duration T1 is equal to 4 hours, the step down period is equal to 1 hour, and so forth.

As illustrated in FIG. 3, once the triggered overdrive pacing parameters have been determined, Step 426, triggered overdrive pacing is turned on and triggered overdrive pacing ON-clock 256 is started, Step 430, and the process waits for a next event to occur in Step 400. At the same time, once triggered overdrive pacing is turned on in Step 430, monitor/controller 250 continuously monitors sensing parameters, such as hemodynamics, ischemia and arrhythmic parameters, for example, in order to determine if the triggered overdrive pacing needs to be adjusted or terminated, as described below.

Figure 10:
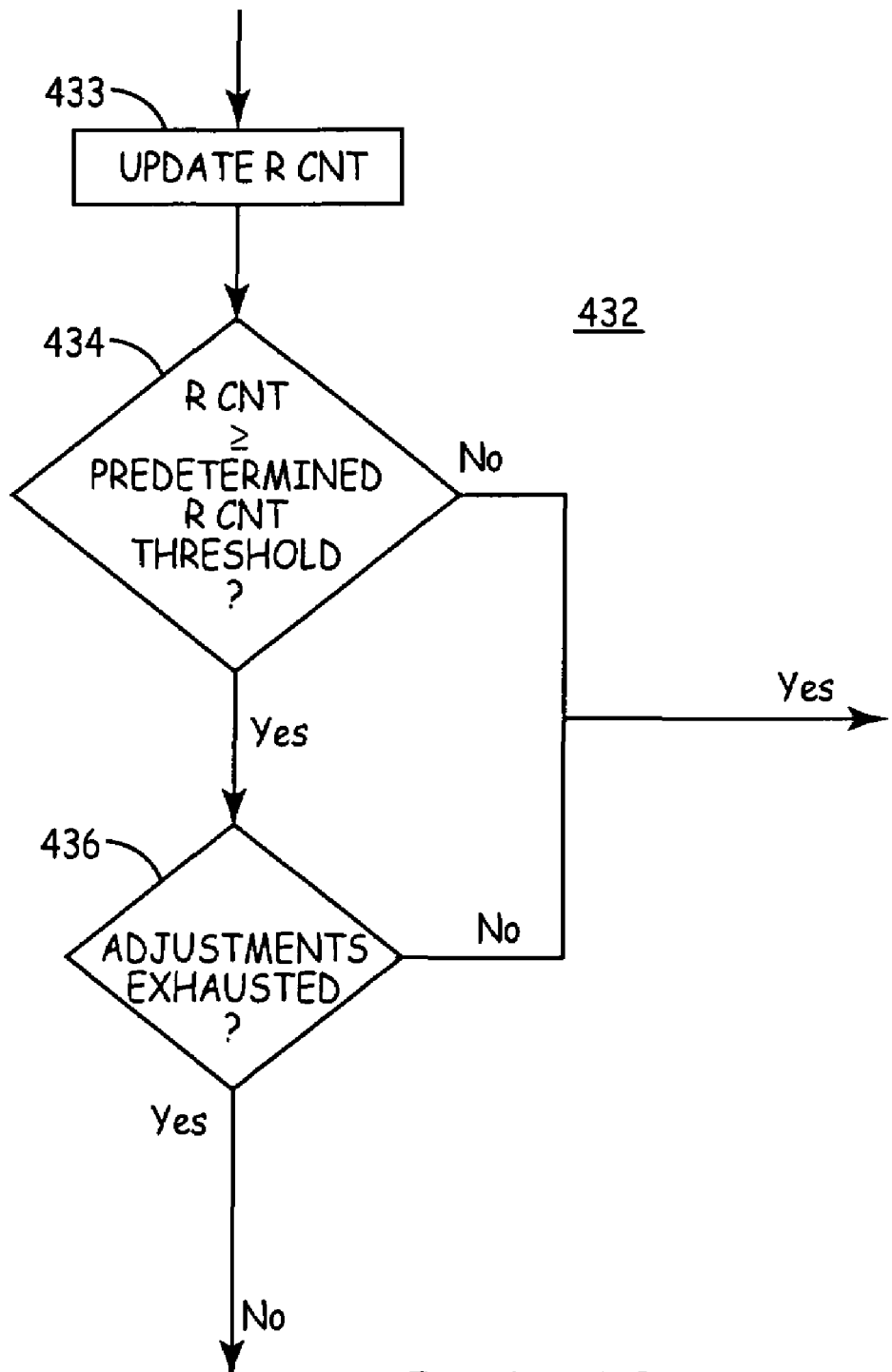
FIG. 10 is a schematic diagram of determining whether to deactivate triggered overdrive pacing according to the present invention.

FIG. 10 is a schematic diagram of determining whether to deactivate triggered overdrive pacing according to the present invention. As illustrated in FIGS. 3 and 10, once triggered overdrive pacing has been turned on, Step 430, and a next event is subsequently detected, Step 400, the process continues as described above. However, since triggered overdrive pacing is determined to be turned on in Step 408, the process then makes a determination as to whether triggered overdrive pacing should be deactivated, Step 432.

Once triggered overdrive pacing is turned on in Step 430, TOP monitor/controller begins counting, using risk counter 254, the number of events that have occurred during prior or current triggered overdrive pacing intervals to determine a risk count (R CNT). As a result, when the next event occurs subsequent to triggered overdrive pacing being turned on, counter 254 is updated, Step 433, and a determination is made as to whether the risk count is greater than a predetermined risk count threshold, Step 434. According to the present invention, the predetermined risk count threshold is set equal to three events, although it is understood that the value chosen for the risk count threshold is a mere design choice and therefore could be set any appropriate value, which may be dependent upon, various factors, such as the value chosen for the duration T1 of the triggered overdrive pacing, for example.

If it is determined that the risk count is not greater than the predetermined risk count threshold, the process waits for a next detected event to occur in Step 400. However, if the risk count is greater than the predetermined risk count threshold, a determination is made as to whether all triggered overdrive pacing adjustments have been exhausted, Step 436.

According to the present invention, adjustments to the triggered overdrive pacing include adjustment of the overdrive pacing rate PR, the overdrive pacing duration T1, or the ramp off duration T2, or a combination thereof. For example, according to the present invention, if triggered overdrive pacing failed to prevent a subsequent VT/VF/NSVT episode and coupled premature ventricular contractions were associated with the initiation of the episode, the triggered overdrive pacing rate could be increased. For example, if VT/VF/NSVT episodes occurred immediately following the triggered overdrive pacing duration T1 of after ramp off period T2, either of these durations T1 or T2 may be increased. As a further example, if a VT/VF/NSVT episode occurred during triggered overdrive pacing and ischemia was noted during triggered overdrive pacing, the triggered overdrive pacing rate might be reduced so as to avoid ischemia development with triggered overdrive pacing, and so forth.

If all adjustments have not been made, the process returns to Step 400 and waits for the next detected event to occur. On the other hand, if all adjustments have been made, triggered overdrive pacing is deactivated, Step 438, and therefore stopped.

Once triggered overdrive pacing is deactivated in Step 438, a determination is made as to whether to reactivate triggered overdrive pacing, Step 440. In a preferred embodiment of the present invention, the determination of whether to reactivate triggered overdrive pacing is made based upon the amount of time that the triggered overdrive pacing has been deactivated so that a determination is made in Step 440 as to whether the amount of time that triggered overdrive pacing has been deactivated exceeds a predetermined time period. Once the predetermined time period is exceeded, triggered overdrive pacing is reactivated, Step 440, and the process waits for a next event to occur in Step 400.

According to an alternate embodiment of the present invention, the determination of whether to reactivated triggered overdrive pacing is made based upon continuous examination by monitor/controller 250 of ongoing rates/intervals, ischemia, and so forth, during normal rhythm and also during a new event or cluster. If monitor/controller 250 determines that certain VT/VF precursors or event characteristics differ from those seen during prior failed triggered overdrive pacing interventions, trigger overdrive pacing is reactivated. For example, if RR intervals prior to a new event showed evidence of long-short-long behavior while RR intervals prior to failed triggered overdrive pacing interventions show only short intervals, triggered overdrive pacing would be reactivated.

According to yet another alternate embodiment of the present invention, the determination as to whether to reactivate triggered overdrive pacing, Step 440, includes a combination of the amount of time that triggered overdrive pacing has been deactivated and whether certain VT/VF precursors or event characteristics differ from those seen during prior failed triggered overdrive pacing interventions. In this way, the determination as to whether to reactivate triggered overdrive pacing is intended to include the use of any number of decision parameters.

Although the present invention is described above in reference to a single ventricular lead in FIG. 1, it is understood that the method and apparatus of the present invention is not intended to be utilized in conjunction with a single ventricular lead, and therefore it is envisioned that the method and apparatus of the present invention may be utilized in conjunction with other implantable medical device systems that include single or multiple leads in both the right and left ventricle. For example, triggered overdrive pacing according to the present invention may be delivered on a single ventricular lead, a multiple but solely ventricular lead system, or both right and left ventricle where right and left ventricle timing is adjusted relative to each other to achieve maximum preventive effect. Atrial pacing may also be used in conjunction with single left ventricle and/or right ventricle pacing to achieve optimal preventative effects, and so forth.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is set forth in the claims below.

What is claimed is:

1. An implantable medical device, comprising:
   a microprocessor characterizing cardiac activity of a patient, the implantable medical device delivering therapy in response to an identified arrhythmia event; and
   a monitor/controller monitoring the characterized cardiac activity and the delivered therapy, determining inter-detection intervals between two or more terminated identified arrhythmia events and controlling subsequent activation of triggered overdrive pacing in response to the determined inter-detection intervals, wherein the monitor/controller determines whether an arrhythmia event has terminated in response to the delivered therapy, determines whether to terminate triggered overdrive pacing in response to triggered overdrive pacing being active, determines whether the arrhythmia event is associated with an arrhythmia cluster in resoonse to the determined inter-detection intervals and triggered overdrive pacing not being active, and activates triggered overdrive pacing in response to the arrhythmia event being associated with an arrhythmia cluster and triggered overdrive pacing being appropriate, and wherein the monitor/controller determines that the arrhythmia event is associated with an arrhythmia cluster in response to an inter-detection interval associated with the arrhythmia event being less than a predetermined time period, a predetermined number of arrhymia events being detected and inter-detection intervals associated with the redetermined number of arrhythmia events corresponding to an arrhythmia cluster.

2. The implantable medical device of claim 1, further comprising an ischemia detector detecting whether ischemia is present in the patient, wherein the monitor/controller determines that triggered overdrive pacing is appropriate in response to a heart rate of the patient being less than a predetermined heart rate threshold and isohemia not being present.

3. The implantable medical device of claim 1, further comprising an ischemia detector detecting whether ischemia is present in the patient, wherein the monitor/controller determines that triggered overdrive pacing is appropriate in response to one of a heart rate of the patient being less than a first predetermined heart rate threshold and ischemia not being present, and the heart rate of the patient being less than the first predetermined heart rate threshold, ischemia being present, and the heart rate being less than a second predetermined heart rate threshold.

4. The implantable medical device of claim 1, wherein the monitor/controller determines one or more of a triggered overdrive pacing rate, a triggered overdrive pacing duration, and a step down period.

5. The implantable medical device of claim 4, further comprising a hemodynamic detector detecting hemodynamics of the patient, wherein, the triggered overdrive pacing rate is dynamically adjusted by the monitor/controller, prior to activating the triggered overdrive pacing subsequent to the delivered therapy, based on one of a percentage of a patients heart rate, prior success of triggered overdrive pacing, and the detected hemodynamics of the patient.

6. The implantable medical device of claim 4, wherein the monitor/controller determines, prior to activating the triggered overdrive pacing subsequent to the delivered therapy, that the triggered overdrive pacing duration as being one of a predetermined time period, automatically adjusted based on prior triggered overdrive pacing, automatically adjusted based on events during or subsequent to the step down period, and a percentage of inter-detection intervals between detected arrhythmia events.

7. The implantable medical device of claim 4, wherein the step down period is calculated as a fraction of a time duration for performing triggered overdrive pacing.

8. An implantable medical device, comprising:
   a microprocessor characterizing cardiac activity of a patient, the implantable medical device delivering therapy in response to an identified arrhythmia event; and
   a monitor/controller monitoring the characterized cardiac activity and the delivered therapy, and controlling activation of triggered overdrive pacing subsequent to the delivered therapy, wherein the monitor/controller determines whether an arrhythmia event has terminated in response to the delivered therapy, determines whether to terminate triggered overdrive pacing in response to triggered overdrive pacing being active, determines whether the arrhythmia event is associated with an arrhythmia cluster in response to triggered overdrive pacing not being active, and activates triggered overdrive pacing in response to the arrhythmia event being associated with an arrhythmia cluster and triggered overdrive pacing being appropriate, the monitor/controller determines one or more of a triggered overdrive pacing rate, a triggered overdrive pacing duration, and a step down period, and the monitor/controller determines whether to terminate friggered overdrive pacing by counting the number of events that have occurred during prior or current triggered overdrive pacing intervals to determine a risk count, determines whether the risk count is greater than a predetermined risk count threshold, and determines whether triggered overdrive pacing adjustments have been exhausted in response to the risk count being greater than the predetermined risk count threshold.

9. The implantable medical device of claim 8, wherein the monitor/controller determines, in response to terminating triggered overdrive pacing, whether to reactivate triggered overdrive pacing.

10. The implantable medical device of claim 9, wherein the monitor/controller determines whether to reactivate triggered overdrive pacing based on one or more of determining whether triggered overdrive pacing has been terminated for a predetermined time period, determining ongoing cardiac activity during normal heart rhythm and during a new event and a new arrhythmia cluster, and determining whether predetermined precursors or events characteristics differ from corresponding predetermined precursors or events characteristics during prior failed triggered overdrive pacing interventions.

11. The implantable medical device of claim 8, wherein the triggered overdrive pacing adjustments include one or more of a triggered overdrive pacing rate, a triggered overdrive pacing threshold, and a step down period.

12. A method for detecting arrhythmias in an implantable medical device, comprising the steps of:
   determining whether an arrhythmia event has terminated in response to a delivered therapy;
   determining whether triggered overdrive pacing is active;
   determining whether to terminate triggered overdrive pacing in response to triggered overdrive pacing being active;
   determining whether the arrhythmia event is associated with an arrhythmia cluster in response to triggered overdrive pacing not being active;
   determining whether triggered overdrive pacing is appropriate; and
   delivering triggered overdrive pacing in response to the arrhythmia event being associated with an arrhythmia cluster and triggered overdrive pacing being appropriate, wherein the step of determining whether to terminate triggered overdrive pacing comprises the steps of:
   counting the number of events that have occurred during prior or current triggered overdrive pacing intervals to determine a risk count;
   determining whether the risk count is greater than a predetermined risk count threshold; and
   determining whether triggered overdrive pacing adjustments have been exhausted in response to the risk count being greater than the predetermined risk count threshold.

13. The method of claim 12, wherein the step of determining whether to terminate triggered overdrive pacing includes the step of determining, in response to determining to terminate triggered overdrive pacing, whether to reactivate triggered overdrive pacing.

14. The method of claim 13, wherein the step of determining whether to reactivate triggered overdrive pacing includes one or more of determining whether triggered overdrive pacing has been terminated for a predetermined time period, determining ongoing cardiac activity during normal heart rhythm and during a new event and a new arrhythmia cluster, and determining whether predetermined precursors or events characteristics differ from corresponding predetermined precursors or events characteristics during prior failed triggered overdrive pacing interventions.

15. The method of claim 12, wherein the triggered overdrive pacing adjustments include one or more of a triggered overdrive pacing rate, a triggered overdrive pacing threshold, and a step down period.

16. An implantable medical device, comprising:
   a microprocessor characterizing cardiac activity of a patient, the implantabie medical device delivering therapy in response to an identified arrhythmia event;
   a monitor/controller monitoring the characterized cardiac activity and the delivered therapy, and controlling activation of triggered overdrive pacing subsequent to the delivered therapy, the monitor/controller determining, prior to activation of triggered overdrive pacing, one or more of a triggered overdrive pacing rate, a triggered overdrive pacing duration, and a step down period;
   an ischemia detector detecting whether isohemia is present in the patient; and
   a hemodynamics detector detecting hemodynamics of the patient, wherein the monitor/controller determines whether an arrhythmia event has terminated in response to the delivered therapy, determines whether to terminate triggered overdrive pacing in response to triggered overdrive pacing being active, determines whether the arrhythmia event is associated with an arrhythmia cluster in response to triggered overdrive pacing not being active, and activates triggered overdrive pacing in response to the arrhythmia event being associated with an arrhythmia cluster and triggered overdrive pacing being appropriate, wherein the monitor/controller determines that triggered overdrive pacing is appropriate in response to a heart rate of the patient being less than a first predetermined threshold and ischemia not being present, and wherein, prior to activating the triggered overdrive pacing, the triggered overdrive pacing rate is dynamically adjusted by the monitor/controller based on one of a percentage of a patient's heart rate, prior success of triggered overdrive pacing, and the detected hemodynamics of the patient, the triggered overdrive pacing duration is determined as being one of a predetermined time period, automatically adjusted based on prior triggered overdrive pacing, automatically adjusted based on events during or subsequent to the step down period, and a percentage of inter-detection intervals between detected arrhythmia events, and the step down period is calculated as a fraction of a time duration for performing triggered overdrive pacing, wherein the monitor/controller determines whether to terminate triggered overdrive pacing by counting the number of events that have occurred during prior or current triggered overdrive pacing intervals to determine a risk count, determining whether the risk count is greater than a predetermined risk count threshold, and determining whether triggered overdrive pacing adjustments have been exhausted in response to the risk count being greater than the predetermined risk count threshold.

17. The implantable medical device of claim 16, wherein the monitor/controller determines, in response to terminating triggered overdrive pacing, whether to reactivate triggered overdrive pacing.

18. The implantable medical device of claim 17, wherein the monitor/controller determines whether to reactivate triggered overdrive pacing based on one or more of determining whether triggered overdrive pacing has been terminated for a predetermined time period, determining ongoing cardiac activity during normal heart rhythm and during a new event and a new arrhythmia cluster, and determining whether predetermined precursors or events characteristics differ from corresponding predetermined precursors or events characteristics during prior failed triggered overdrive pacing interventions.

19. The implantable medical device of claim 18, wherein the triggered overdrive pacing adjustments include one or more of a triggered overdrive pacing rate, a triggered overdrive pacing threshold, and a step down period.

* * * * *

UNITED STATES PATENT AND TRADEMARK OFFICE
CERTIFICATE OF CORRECTION

PATENT NO. : 7,076,298 B2
APPLICATION NO. : 10/171231
DATED : July 11, 2006
INVENTOR(S) : Vasant Padmanabhan et al.

It is certified that error appears in the above-identified patent and that said Letters Patent is hereby corrected as shown below:

Col. 20, line 23, please delete "isohemia" and insert --ischemia--.

Col. 21, line 15, please delete "friggered" and insert --triggered--.

Col. 22, line 35, please delete "isohemia" and insert --ischemia--.

Signed and Sealed this

Second Day of January, 2007

JON W. DUDAS
*Director of the United States Patent and Trademark Office*